(12) United States Patent
Baley et al.

(10) Patent No.: US 7,608,761 B2
(45) Date of Patent: *Oct. 27, 2009

(54) METHOD FOR DISEASE CONTROL IN MON89788 SOYBEAN

(75) Inventors: George Jamie Baley, Webster Groves, MO (US); Frank C. Kohn, St. Louis, MO (US); John W. Pitkin, Wildwood, MO (US); Jennifer Rinehart, Spring Green, WI (US); Jeremey H. Taylor, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 200 days.

This patent is subject to a terminal disclaimer.

(21) Appl. No.: 11/441,918

(22) Filed: May 26, 2006

(65) Prior Publication Data

US 2006/0288447 A1 Dec. 21, 2006

Related U.S. Application Data

(60) Provisional application No. 60/685,584, filed on May 27, 2005.

(51) Int. Cl.
*A01H 5/00* (2006.01)
(52) U.S. Cl. .................................................. 800/300
(58) Field of Classification Search ........................ None
See application file for complete search history.

(56) References Cited

U.S. PATENT DOCUMENTS

| | | | |
|---|---|---|---|
| 4,535,060 A | 8/1985 | Comai | 435/172.3 |
| 5,094,945 A | 3/1992 | Comai | 435/172.3 |
| 5,110,805 A | 5/1992 | Berner et al. | 514/76 |
| 5,310,667 A | 5/1994 | Eichholtz et al. | 435/91.1 |
| 5,312,910 A | 5/1994 | Kishore et al. | 536/23.2 |
| 5,437,697 A | 8/1995 | Sebastian et al. | 47/58 |
| 5,463,175 A | 10/1995 | Barry et al. | 800/300 |
| 5,554,798 A | 9/1996 | Lundquist et al. | 800/300.1 |
| 5,627,061 A | 5/1997 | Barry et al. | 800/288 |
| 5,633,435 A | 5/1997 | Barry et al. | 800/288 |
| 5,659,114 A | 8/1997 | Paschall | 800/312 |
| 5,804,425 A | 9/1998 | Barry et al. | 435/193 |
| 6,040,497 A | 3/2000 | Spencer et al. | 800/278 |
| 6,083,878 A | 7/2000 | Brants et al. | 504/206 |
| 6,248,876 B1 | 6/2001 | Barry et al. | 536/24.3 |
| 6,462,258 B1 | 10/2002 | Fincher et al. | 800/300 |
| 6,573,425 B1 | 6/2003 | Baszczynski et al. | 800/278 |
| 6,610,910 B1 | 8/2003 | Streit et al. | 800/312 |
| 6,660,911 B2 | 12/2003 | Fincher et al. | 800/300 |
| 6,689,880 B2 | 2/2004 | Chen et al. | 536/24.3 |
| 6,733,974 B1 | 5/2004 | Feazel | 435/6 |
| 6,740,488 B2 | 5/2004 | Rangwala et al. | 435/6 |
| 6,818,807 B2 | 11/2004 | Trolinder et al. | 800/300 |
| 6,825,400 B2 | 11/2004 | Behr et al. | 800/300.1 |
| 6,893,826 B1 | 5/2005 | Hillyard et al. | 435/6 |
| 6,900,014 B1 | 5/2005 | Weston et al. | 435/6 |
| 6,919,495 B2 | 7/2005 | Fincher et al. | 536/23.2 |
| 2002/0133852 A1 | 9/2002 | Hauge et al. | 702/19 |
| 2003/0060371 A1 | 3/2003 | Asrar et al. | 504/272 |
| 2003/0083480 A1 | 5/2003 | Castle et al. | 536/23.1 |
| 2003/0114308 A1 | 6/2003 | DeBillot et al. | 504/116.1 |
| 2004/0018518 A1 | 1/2004 | Krieb et al. | 435/6 |
| 2004/0177399 A1 | 9/2004 | Hammer et al. | 800/278 |
| 2005/0223425 A1 | 10/2005 | Clinton et al. | 800/279 |
| 2005/0233905 A1 | 10/2005 | DeBillot et al. | 504/102 |
| 2005/0246798 A1 | 11/2005 | Castle et al. | 800/300 |
| 2006/0021093 A1 | 1/2006 | Hammer et al. | 800/300 |
| 2006/0021094 A1 | 1/2006 | Hammer et al. | 800/300 |
| 2006/0111239 A1 | 5/2006 | Oakley et al. | 504/116 |
| 2006/0223707 A1 | 10/2006 | Baley et al. | 504/165 |
| 2006/0282911 A1 | 12/2006 | Bull et al. | 800/266 |
| 2006/0282915 A1 | 12/2006 | Malven et al. | 800/278 |
| 2006/0288447 A1 | 12/2006 | Baley | 800/279 |
| 2007/0010401 A1 | 1/2007 | Noon et al. | 504/127 |
| 2007/0197474 A1 | 8/2007 | Clinton et al. | 504/206 |

FOREIGN PATENT DOCUMENTS

| | | |
|---|---|---|
| CA | 2611178 | 12/2007 |
| DE | 100 59 609 | 6/2002 |
| WO | WO 92/00377 | 1/1992 |
| WO | WO 99/23232 | 5/1999 |
| WO | WO 99/31964 | 7/1999 |
| WO | WO 01/49104 | 7/2001 |
| WO | WO 02/06500 | 1/2002 |

(Continued)

OTHER PUBLICATIONS

Sanogo et al 2000, Phytopathology 90(1): 57-66.*
U.S. Appl. No. 11/441,914, filed May 26, 2006, Malven et al.
U.S. Appl. No. 11/638,450, filed Dec. 14, 2006, Clinton et al.
Anderson et al., "Rust control in glyphosate tolerant wheat following application of the herbicide glyphosate," *Plant Disease*, 89(11):1136-1142, 2005.
Feng et al., "Glyphosate inhibits rust diseases in glyphosate-resistant wheat and soybean," *PNAS*, 102(48):17290-17295, 2005.
Franz et al., "Glyphosate: a unique global herbicide," *American Chemical Society*, Chapter 5:103-141, 1997.
Grossbard, "Effects of glyphosate on the microflora: with reference to the decomposition of treated vegetation and interaction with some plant pathogens," Chapter 11 in The Herbicide Glyphosate, Grossbard et al. ed. , 159-165, 178-182, 1985.

(Continued)

*Primary Examiner*—David H Kruse
(74) *Attorney, Agent, or Firm*—Lawrence M. Lavin, Jr.; Sonnenschein Nath & Rosenthal LLP

(57) ABSTRACT

The present invention relates to a method to control diseases of MON89788 soybean by treatment with formulations and mixtures containing glyphosate. In particular, the formulations and mixtures are effective at controlling fungal diseases of MON89788. More specifically, the invention relates to a method to control the severity of leaf rust disease on MON89788.

15 Claims, 2 Drawing Sheets

FOREIGN PATENT DOCUMENTS

| WO | WO 02/44407 | 6/2002 |
|---|---|---|
| WO | WO 03/013224 | 2/2003 |
| WO | WO 2004/043150 | 5/2004 |
| WO | WO 2004/072235 | 8/2004 |
| WO | WO 2005/041669 | 5/2005 |
| WO | WO 2005/102057 | 11/2005 |
| WO | WO 2006/130436 | 12/2006 |
| WO | WO 2006/131230 | 12/2006 |
| WO | WO 2007/017256 | 2/2007 |
| WO | WO 2008/116730 | 10/2008 |
| WO | WO 2008/129060 | 10/2008 |

OTHER PUBLICATIONS

Ramsdale et al., "Glyphosate tank-mixed with insecticides or fungicides," *North Central Weed Science Society*, 59:280-283, 2002.

Abremski et al., "Studies on the properties of P1 site-specific recombination: evidence for topologically unlinked products following recombination," *Cell*, 32:1301-1311, 1983.

Axelos et al., "The gene family encoding the arabidopsis thaliana translation elongation factor EF-1 alpha: molecular cloning, characterization and expression," *Mol. Gen Genet*, 219(1- 2):106-112, 1989.

Barker et al., "Nucleotide sequence of the T-DNA region from the agrobacterium tumefaciens octopine Ti plasmid pTi15955," *Plant Mol. Biol.*, 2:335-350, 1983.

Chevalier et al., "Design, activity, and structure of a highly specific artificial endonuclease," *Molecular Cell*, 10:895-905, 2002.

Coruzzi et al., "Tissue-specific and light-regulated expression of pea nuclear gene encoding the small subunit of ribulos-1,5-bisphosphate caroxylase," *EMBO J.*, 3:1671-1679, 1984.

Dempster et al., "Maximum likelihood from incomplete data via the EM algorithm," *J. R. Stat. Soc.*, 39B:1-38, 1977.

Depicker et al., "Nopaline synthase: transcript mapping and DNA sequence," *J. Mol. Appl. Genet*, 1(6):561-573, 1982.

Excoffier and Slatkin, "Maximum-likelihood estimation of molecular haplotype frequencies in a diploid population," *Biol. Evol.*, 12(5):921-927, 1995.

Harrison et al., "The expressed protein in glyphosate-tolerant soybean, 5-enolpyruvylshikimate-3-phosphate synthase from agrobacterium sp. strain CP4, is rapidly digested in vitro and is not toxic to acutely gavaged mice,"*J. Nutr.*, 126(3):728-740, 1996.

Hernandez et al., "Development of melting temperature-based SYBR green I polymerase chain reaction methods for multiplex genetically modified organism detection," *Analytical Biochemistry*, 323(2):164-170, 2003.

Klee et al., "Cloning of an arabidopsis thaliana gene encoding 5-enolpyruvylshikimate-3-phosphate synthase: sequence analysis and manipulation to obtain glyphosate-tolerant plants,"*Mol. Gen Genet*, 210(3):437-442, 1987.

Lloyd et al., "Targeted mutagenesis using zinc-finger nucleases in arabidopsis," *Proc. Natl. Acad. Sci.*, 102(6):2232-2237, 2005.

McCallum et al., "Targeting induced local lesions in genomes (TILLING) for plant functional genomics," *Plant Physiol.*, 123:439-442, 2000.

Monsanto Company, "Application for authorization to place on the market MONS 89788 soybean in the European Union, according to regulation (EC) No. 1829/2003 on genetically modified food and feed—Part II—Summary," Summary of the Dossier EFSA GMO NL 2006-36, pp. 1-31, 2006.

Office Action regarding U.S. Appl. No. 11/441,914, filed Sep. 2, 2008.

Office Action regarding U.S. Appl. No. 11/441,915, filed Oct. 20, 2008.

Padgette et al., "Development, identification, and characterization of a glyphosate-tolerant soybean line," *Crop Sci.*, 35:1451-1461, 1995.

Padgette et al., "Site-directed mutagenesis of a conserved region of the 5-enolpyruvylshikimate-3-phosphate synthase active site," *J. Biological Chemistry*, 266(33):22364-22369, 1991.

PCT International Search Report for PCT/US2006/020323, Jan. 2, 2007.

Richins et al., "Sequence of figwort mosaic virus DNA (caulimovirus group)," *Nucleic Acids Res.*, 15(20):8451-466, 1987.

Rott et al., "Detection and quantification of roundup ready soy in foods by conventional and real-time polymerase chain reaction," *Journal of Agricultural and Food Chemistry*, 52(16):5223-5232, 2004.

Smith et al., "A combinatorial approach to create artificial homing endonucleases cleaving chosen sequences," *Nucleic Acids Res.*, 34(22):1-12, 2006.

Song et al., "A new integrated genetic linkage map of the soybean," *Theor. Appl. Genetics*, 109:122-128, 2004.

Sternberg et al., "Site-specific recombination and its role in the life cycle of bacteriophage P1," Cold Spring Harbor Symp. Quant. Biol., 45:297-309, 1981.

Terry et al., "Event-specific detection of roundup ready soya using two different real time PCR detection chemistries," *Eur. Food Res. Technol.*, 213:425-431, 2001.

Windels et al., "Characterization of the roundup ready soybean insert," *Eur. Food Res. Technol.*, 213(2):107-112, 2001.

Windels et al., "Development of a line specific GMO detection method: a case study," *Me. Fac. Ladbouww. Univ. Gent.*, 65(5b):459-462, 1999.

Wright et al., "High-frequency homologous recombination in plants mediated by zinc-finger nucleases," *Plant J.*, 44:693-705, 2005.

Berner et al., "Effects of glyphosate on calonectria crotalariae and red crown rot of soybean," *Plant Disease*, 75(8):809-813, 1991.

Bradley et al., "Influence of glyphosate and fungicide coapplications on weed control, spray penetration, soybean response, and yield in glyphosate-resistant soybean," *Agronomy J.*, 100:1360-1365, 2008.

Feng et al., "Disease control activities of glyphosate in glyphosate-resistant crops," American Chemical Society, 233$^{rd}$ National Meeting and Exposition, Chicago, IL, Picogram 72:81, Mar. 25-29, 2007.

Feng et al., "The control of asian rust by glyphosate in glyphosate-resistant soybeans," *Pest Manag. Sci.*, 64:353-359, 2008.

Lee et al., "Glyphosate and shade effects on glyphosate-resistant soybean defense response to sclerotinia sclerotiorum," *Weed Sci.*, 51(3):294-298, 2003.

Njiti et al., "Roundup ready soybean: glyphosate effects on fusarium solani root colonization and sudden death syndrome," *Agronomy J.*, 95(5):1140-1145, 2003.

Powell et al., "A critique of studies evaluating glyphosate effects on diseases associated with fusarium spp.," *Weed Res.*, 48(4):307-318, 2008.

Sanogo et al., "Field response to glyphosate-tolerant soybean to herbicides and sudden death syndrome," *Plant Disease*, 85(7):773-779, 2001.

Yang, "Soybean (Glycine max) response to glyphosate and soybean cyst nematode (Heterodera glycines)," *Weed Technology*, 16:332-339, 2002.

\* cited by examiner

US 7,608,761 B2

METHOD FOR DISEASE CONTROL IN MON89788 SOYBEAN

This application claims priority from U.S. Provisional Application No. 60/685,584, filed May 27, 2005, the entire disclosure of which is herein incorporated by reference.

BACKGROUND OF THE INVENTION

1. Field of the Invention

The present invention relates to the field of chemical disease control. More specifically, the invention relates to a method for controlling diseases of soybean by the application of glyphosate or mixtures of glyphosate and a fungicide to a glyphosate tolerant soybean MON89788.

2. Description of Related Art

The soybean, *Glycine max* (L.) Merril, is one of the major economic crops grown worldwide as a primary source of vegetable oil and protein (Sinclair and Backman, 1989). The growing demand for low cholesterol and high fiber diets has also increased soybean's importance as a health food.

Soybean yields in the United States are reduced each year by diseases. High yields per hectare are critical to a farmer's profit margin, especially during periods of low prices for soybean. The financial loss caused by soybean diseases is important to rural economies and to the economies of allied industries in urban areas. The effects of these losses are eventually felt throughout the soybean market worldwide. Estimates of loss due to disease in the United States and Ontario vary from year to year and by disease. From 1999 to 2002 soybean yield loss estimates were in the range of 8 million metric tons to 10 million metric tons in the United States and 90,000 to 166,000 metric tons in Ontario (Wrather et al, 2003).

Asian Soybean Rust (herein referred to as ASR) has been reported in the Eastern and Western Hemispheres. In the Eastern Hemisphere, ASR has been reported in Australia, China, India, Japan, Taiwan and Thailand. In the Western Hemisphere, ASR has been observed in Brazil, Colombia, Costa Rica, Puerto Rico among other places. ASR can be a devastating disease, causing yield losses of up to 70 to 80% as reported in some fields in Taiwan. Plants that are heavily infected have fewer pods and smaller seeds that are of poor quality (Frederick et al, 2002). ASR was first observed in the United States in Hawaii in 1994. ASR was later introduced into the continental United States in the fall of 2004, presumably as a consequence of tropical storm activity. Model predictions indicated that ASR had been widely dispersed throughout the southeastern United States, and subsequent field and laboratory observations confirmed this distribution.

N-phosphonomethylglycine, also known as glyphosate, is a well-known herbicide that has activity on a broad spectrum of plant species. Glyphosate is the active ingredient of Roundup® (Monsanto Co., St. Louis, Mo.), a safe herbicide having a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants.

Glyphosate tolerance can be achieved by the expression of EPSPS variants that have lower affinity for glyphosate and therefore retain their catalytic activity in the presence of glyphosate (U.S. Pat. Nos. 5,633,435; 5,094,945; 4,535,060; and 6,040,497). Such genes are used for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (U.S. Pat. No. 6,689,880), cotton (U.S. Pat. No. 6,740,488), soybean (WO 9200377) and canola (US 20040018518). The treatment of glyphosate tolerant crop plants with glyphosate has been shown to reduce disease incidence or severity (US 2005000654442 and US 2003000532758, both herein incorporated by reference).

This invention provides a method for treatment of a new glyphosate tolerant soybean event MON89788 (also referred to as MON19788 or GM A19788) with glyphosate to control various fungal diseases, especially Asian Soybean Rust disease.

SUMMARY OF THE INVENTION

The present invention relates to a method for controlling diseases of a soybean transgenic event designated MON89788 and progeny thereof having representative seed deposited with American Type Culture Collection (ATCC) with accession No. PTA-6708. The method for preventing a disease in a soybean plant comprises (a) identifying a soybean plant as being at risk of disease caused by a plant pathogen, wherein the soybean plant is identified as event MON89788 comprising a transgene that encodes a polypeptide that confers plant tolerance to glyphosate; and (b) applying a formulation or mixture comprising glyphosate to the soybean plant, whereby the disease is prevented in the MON89788 soybean plant. In another aspect of the invention, weeds and disease are controlled in a field of MON89788 by application of glyphosate.

The present invention also provides a method for treating a root, stem, leaf, pod or seed fungal disease in a MON89788 soybean plant comprising, identifying a MON89788 soybean plant as being infected with a fungal disease, and applying a composition comprising glyphosate to the soybean plant or portion thereof, whereby the composition results in the disease being controlled. In another aspect of the invention, the treatment is a mixture having a glyphosate and a fungicide composition applied to the soybean plant or portion thereof, whereby the treatment results in the root, stem, leaf, pod or seed disease being controlled.

The present invention also provides a method for treating a foliar fungal disease in a MON89788 soybean plant comprising: identifying a MON89788 soybean plant as being infected with a foliar fungal disease, and applying a composition comprising glyphosate to the soybean plant or portion thereof, whereby the composition results in the disease being controlled. In another aspect of the invention, the treatment is a mixture comprising glyphosate and a fungicide composition applied to the soybean plant or portion thereof, whereby the treatment results in the foliar disease being controlled.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
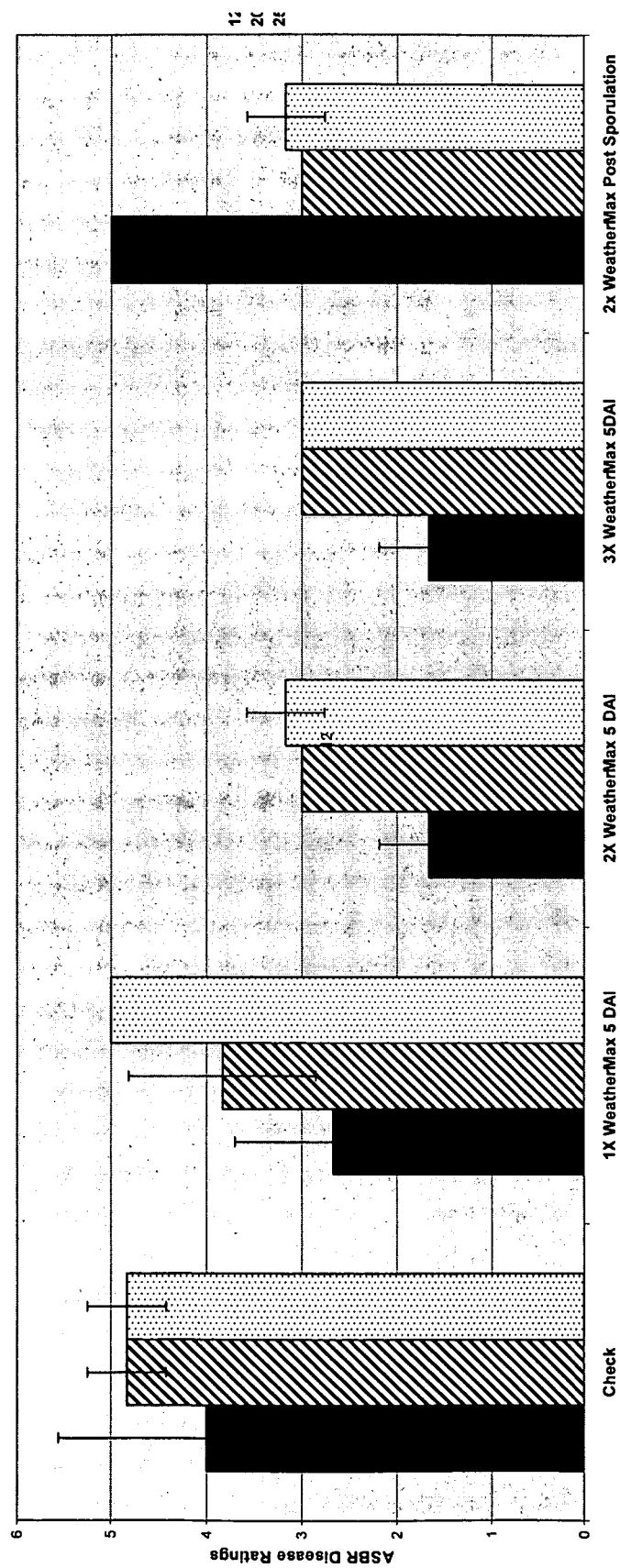
FIG. 1. Results from detached soybean leaf assay described in Example 1.
Figure 2:
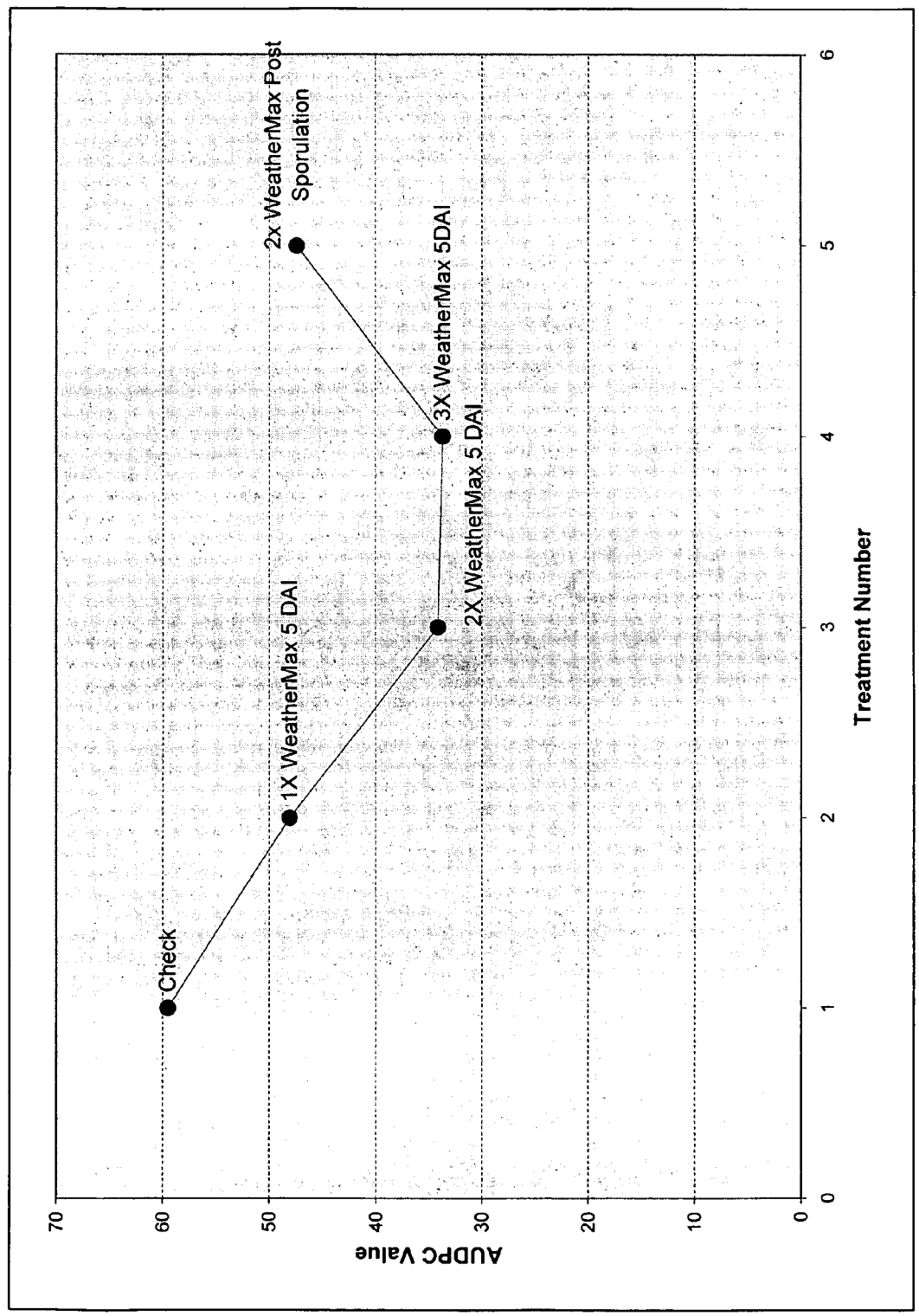
FIG. 2. Area Under the Disease Progress Curve (AUDPC) analysis of material described in FIG. 1.

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Rieger et al. (1991) and Lewin (1994). The nomenclature for DNA bases as set forth at 37 CFR § 1.822 is used.

As used herein, the term "soybean" means *Glycine max*, and includes all plant varieties that can be bred with soybean including wild soybean species.

As used herein, the term "comprising" means "including but not limited to".

A transgenic "event" is produced by transformation of a plant cell with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA.

Transgenic events generally have a range of expression of the transgenic trait. It is necessary to select from a large population of transgenic events those that have the desired expression level of the transgene or the desired phenotype. The transgenic soybean event MON89788 was selected from a large number of transformed soybean plants for its superior agronomic performance, especially yield, and additionally MON89788 provides a high level of glyphosate tolerance. This event is particularly useful in the present invention where the rates of glyphosate or the timing of the glyphosate application necessary to control disease can be broadly adapted so as not to substantially affect the agronomic performance of MON89788.

A method of the present invention provides for controlling, preventing or treating diseases of soybean MON89788, especially a disease caused by a member of the Ascomycetes, Deuteromycetes, Basidiomycetes, or Oomycetes, including members of the Uredinales, Ustilaginales, and Erysiphales. Specific diseases of soybean include, but are not limited to Anthracnose (*Colletotrichum dematium*), Brown Leaf Spot (*Septoria glycines*), Charcoal Rot (*Macrophomina phaseolina*), Cotton Root Rot (*Phymatotrichum omnivorum*), Downy Mildew (*Peronospora manshurica*), Powdery Mildew (*Microsphaera diffusa*), Frogeye Leafspot (*Cercospora sojina*), Cercospora leaf blight (*Cercospora carotae*), Pod and Stem Blight (*Diaporthe phaseolorum* var. *sojae*), Purple Seed Stain (*Cercospora kikuchii*), Southern Blight (*Sclerotium roljsii*), Stem Canker (*Diaporthe phaseolorum*var. *caulivora*), Aerial blight (*Rhizoctonia solani*), Target Spot (*Alternaria* sp), and Asian soybean rust (ASR) disease caused by *Phakopsora* species in a glyphosate tolerant soybean plant MON89788. The method provides for the application of a glyphosate containing formulation or mixture to a soybean plant MON89788 that is in need of disease control, prevention or treatment. In another aspect, the treatment is a mixture having a glyphosate and a fungicide composition applied to the soybean plant MON89788 or portion thereof, whereby the mixture results in the disease being controlled.

Two species of fungi, *Phakopsora pachyrhizi* Sydow and *Phakopsora meibomiae* (Arthur) Arthur, herein referred to as *Phakospora* sp., cause ASR. Unlike other rusts, *P. pachyrhizi* and *P. meibomiae* infect an unusually broad range of plant species. *P. pachyrhizi* is known to naturally infect 31 species in 17 genera of legumes and 60 species in 26 other genera have been infected under controlled conditions. *P. meibomiae* naturally infects 42 species in 19 genera of legumes, and 18 additional species in 12 other genera have been artificially infected. Twenty-four plant species in 19 genera are hosts for both species (Frederick et al, 2002).

Glyphosate tolerance is well known and may be imparted to plant species by recombinant DNA techniques that are described in the art (as described for example by U.S. Pat. Nos. 5,312,910; 5,310,667; 5,463,175). Polynucleotide molecules encoding proteins involved in glyphosate herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, U.S. Pat. No. 6,040,497 and in U.S. Pat. No. 5,094,945 for glyphosate tolerance, all of which are hereby incorporated by reference; polynucleotides encoding a glyphosate oxidoreductase, glyphosate-N-acetyl transferase, or glyphosate decarboxylase (GOX, U.S. Pat. No. 5,463,175; GAT, US Patent publications 20030083480 and 20050246798; glyphosate decarboxylase, US Patent publications 20060021093; 20060021094; 20040177399, herein incorporated by reference in their entirety).

"Glyphosate" refers to N-phosphonomethylglycine and its' salts. Glyphosate is the active ingredient of Roundup® herbicide (Monsanto Co., St Louis, Mo.). Plant treatments with "glyphosate" refer to treatments with the Roundup® or Roundup® Ultra herbicide formulation, unless otherwise stated. Glyphosate as N-phosphonomethylglycine and its' salts (not formulated Roundup® herbicide) are components of synthetic culture media used for the selection of bacteria and plant tolerance to glyphosate or used to determine enzyme resistance in in vitro biochemical assays. Examples of commercial formulations of glyphosate include, without restriction, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; ROUNDUP® WEATHERMAX containing the potassium salt, and those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

Application of glyphosate compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one aspect of such techniques, a global positioning system operated with the spraying apparatus can be used to control application of the composition in desired amounts to different parts of a field. A glyphosate composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

A rate of application of a glyphosate composition from about 0.1 pounds acid equivalent/acre (herein referred to as "lb/acre" unless otherwise indicated) to about 5 lb/acre of glyphosate is effective in controlling, preventing or treating a pathogen in accordance with a method of the present invention. Yet more preferable are rates of application ranging from about 0.5 lb/acre to about 2.5 lb/acre. Most preferable are rates of application of about 0.75 lb/acre. Glyphosate may be mixed with fungicides for example, most preferably a glyphosate compound is mixed with a fungicide compound or combinations of fungicides, such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimenol, tricyclazole, trifloxystrobin, triticonazole, validamycin and vinclozolin; combinations of fungicides are common for example, cyproconazole and azoxystrobin, difenoconazole, and metalaxyl-M, fludioxonil and metalaxyl-M, mancozeb and metalaxyl-M, copper hydroxide and metalaxyl-M, cyprodinil and fludioxonil, cyproconazole and propiconazole. Commercially available fungicide formulations include, but are not limited to Quadris® (Syngenta Corp), Bravo® (Syngenta Corp), Echo 720® (Sipcam Agro Inc), Headline® 2.09EC (BASF Corp), Tilt® 3.6EC (Syngenta Corp), PropiMax™ 3.6EC (Dow AgroSciences), Bumper® 41.8EC (MakhteshimAgan), Folicur® 3.6F (Bayer CropScience), Laredo® 25EC (Dow AgroSciences), Laredo™ 25EW (Dow AgroSciences), Stratego® 2.08F (Bayer Corp), Domark™ 125SL (SipcamAgro USA), and Pristine®38% WDG (BASF Corp) that can be combined as mixtures with glyphosate compositions as described in the present invention to provide enhanced protection from fungal disease. When glyphosate is used in mixtures with fungicides or as sequential applications of glyphosate and the fungicide, the rates may be reduced in order to achieve the most efficient ratio of an effective concentration of glyphosate and the fungicide to provide a cost effective disease control mixture. The application of glyphosate and a fungicide may provide a synergistic benefit. A 1×rate of glyphosate (0.75 lb/acre) followed by a 0.5×rate of a fungicide compound will provide equivalent or enhanced fungal disease control as compared to a 2×rate of glyphosate or a 1×rate of a fungicide. It is contemplated that further reductions in application rates using a glyphosate and fungicide admixture will be effective to control different fungal diseases. For example, a 1× rate of glyphosate mixed with a 0.4× rate of fungicide, or 0.3×, or 0.2×, or 0.1× rate or rates in between may be cost effective for the economic control of fungal diseases. Additionally, a reduced rate of glyphosate in the mixture may also provide effective and cost efficient control of fungal diseases. For example, a 0.75× rate of glyphosate with a 0.5× rate of a fungicide, or a 0.5× rate of glyphosate with a 0.5× rate of fungicide, or a 0.25× rate of glyphosate with a 0.5× rate of fungicide, or a 0.1× rate of glyphosate with a 0.5× rate of fungicide. A ratio of 0.1× glyphosate and 0.1× fungicide in an admixture is contemplated in the present invention. The exact ratio can be determined by the effective amount of each compound that is delivered to the diseased or disease susceptible plant tissues and by those skilled in the art of chemical formulation and application for the control of fungal diseases of MON89788 plants.

The present invention also provides for controlling harmful weeds and controlling, preventing or treating pathogens in a field of glyphosate tolerant MON89788 soybean plants wherein the method uses applications of glyphosate compositions. Such methods comprise one or more applications of a glyphosate composition to a field comprising MON89788 plants tolerant or resistant to glyphosate. Two or more glyphosate applications may be performed. The application or applications are timed for effective weed control and effective disease control, and prevention or treatment of disease in the treated plant(s) without affecting the agronomic performance of MON89788. For example, without limitation, a first application of glyphosate is applied at a time when the application controls the weeds within the field of MON89788. For example, without limitation, a second application is at a time when the plants are either at risk of infection or have already been infected by a plant pathogen.

In one aspect, a method for controlling weeds and pathogens in a field of MON89788 soybeans comprises the steps of (a) planting MON89788 seed in a field, (b) substantially freeing the field of non-MON89788 plants by applying a herbicidal composition and (c) thereafter controlling, preventing or treating disease by applying a glyphosate composition. In such a method, it should be appreciated that the steps of planting and substantially freeing can be interchanged. Thus, the field may be substantially free of non-crop plants before planting the crop in the field. In one aspect, the application of the herbicidal composition and the disease control glyphosate application are 1 day apart. Alternatively, they may be 2, 3, 4, 5, 6, 7, 8, 9, 10, 14, or 21 days apart. In another aspect, the herbicidal and pesticidal applications are greater than 5, 10, 20, 25, 30, 35, 40, 45, or 50 days apart.

In one aspect, the glyphosate composition is applied one or more times during the growing season. In another aspect, the glyphosate composition is applied 2, 3, 4, 5, 6, 7, 8, 9, or 10 times during the growing season to a plant in need of disease control, prevention or treatment. In one aspect, the application of a glyphosate composition results in a concentration of glyphosate in a plant tissue of between about 0.01 ppm to about 100 ppm per fresh weight. More preferably, tissue concentrations of between 0.1 ppm and 25 ppm glyphosate of fresh weight are obtained in the tissues of plants treated in the methods of the present invention. Most preferably, concentrations of between about 0.5 ppm and about 10 ppm glyphosate are effective in controlling, preventing or treating disease in a treated MON89788 plant.

The following examples are included to demonstrate aspects of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific aspects which are disclosed and still obtain a like or similar result without departing from the spirit and scope of the invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Growth chamber and greenhouse assays were conducted to determine if glyphosate treatments (Roundup® WeatherMax) decreased the disease severity of Asian Soybean Rust (ASR) on MON89788. Growth chamber assays were conducted following a detached leaf assay method. Plants of MON89788 were grown in the greenhouse and leaves from the 3$^{rd}$ trifoliate were detached and placed in 6-well trays with water. Five treatments were evaluated: (1) an untreated check inoculated with spores of ASR (Loxley Al isolate); (2) leaf tissue of MON89788 inoculated with ASR spores and treated with glyphosate post-sporulation (13 days after inoculation with spores (DAI)); (3) MON89788 treated with 1× rate (0.75 lb/acre) of Roundup® WeatherMax 5 DAI; (4) MON89788 treated with 1× rate of Roundup® WeatherMax 5 DAI; and (5) MON89788 treated with 3× rate of Roundup® WeatherMax 5 DAI. The rust severity score uses a rating scale from 1 to 5; 1—being immune, 2—demonstrating red/brown lesions over less than 50% of the leaf area, 3—demonstrating red/brown lesions over greater than 50% of the leaf area, 4—demonstrating tan lesions over less than 50% of the leaf area and 5-demonstrating tan lesions over greater than 50% of the leaf area.

The leaves were rated for disease severity 12 DAI, 20 DAI, and 25 DAI. FIG. 1 shows a summary of results from the detached leaves untreated or treated 5 DAI with 1×, 2×, or 3× Roundup® WeatherMax. At 12 DAI (solid bar), MON89788 leaves not treated with glyphosate displayed high levels of disease severity and sporulation, whereas leaves treated with 1× rate of Roundup® WeatherMax 5 DAI showed reduced severity. At 20 DAI (hatched bar), 2× and 3× treated leaves continued to show lower levels of ASR compared to untreated checks. The levels of sporulation of ASR on MON89788 leaves were also reduced at 20 DAI (stippled bar) when treated with 2× at 13 DAI.

The analysis of the disease progression is illustrated in FIG. 2 and measured as the Area Under Disease Progress Curve (AUDPC) for the same material summarized in FIG. 1. The AUDPC for MON89788 leaves treated with 2× and 3× rates were lower compared to other treatments. The disease progression was reduced for all glyphosate treatments at 5DAI and the 2× rate post-sporulation.

Greenhouse assays on intact MON89788 plants were treated with 1×, 2×, and 3× rates of Roundup® WeatherMax at 6 DBI (days before inoculation) and 9 DAI. Results for this experiment were collected 17 DAI. All glyphosate treatments, except for the 1× treatment at 6 DBI, resulted in lower levels of ASR infection and disease on MON89788 soybean. The severity of ASR disease was decreased on MON89788 treated with 1× compared to the control, and a further decrease was observed with the 2× and 3× treatments. An additional treatment of 1× at 6 DBI followed by 1× at 9 DAI showed reduction in severity of disease similar to the 2× and 3× treatments applied pre or post-inoculation.

The treatment of MON89788 with glyphosate to control ASR disease was demonstrated in the greenhouse and in growth chamber assays. The pre-inoculation treatments appeared to slow the rate of disease development, whereas the post-disease development/sporulation treatments appeared to arrest sporulation. Applying glyphosate in split treatments (1× pre+1× post-inoculation) reduced levels of ASBR similar to single 2× and 3× pre- or post-inoculation.

Additional tests were conducted to further evaluate the disease preventative activity of glyphosate treatment of MON89788. Seeds of MON89788 were planted and grown to the V4-V5 growth stage then treated with Roundup® WeatherMax at 1×, 2×, and a surfactant control. Twenty-four hours after the glyphosate treatment the first and second trifoliate leaves of each plant were inoculated with approximately 5×10$^4$ ASR spores. Rating of the number and severity of lesions on the lowest trifoliate was conducted beginning 10 DAI, and the evaluations were made every 2 days until 20 DAI.

In the preventative experiment, significant differences were found when comparing disease severity between treatments evaluated on the same day. The 2× treatment had significantly less disease severity than 1× at 16, 20, and 25 DAI. The 2× when compared to the surfactant control at 20 and 25 DAI, also had less disease severity. Infection severity between days within the same treatment was significant.

Example 2

The control of Frogeye Leafspot (*Cercospora sojina*), Cercospora leaf blight (*Cercospora carotae*) and Aerial blight (*Rhizoctonia solani*) was demonstrated on MON89788 soybean. Soybean plants comprising event MON89788 and grown under standard conditions in a greenhouse were treated with 1×, 2× or 3× concentrations of glyphosate and inoculated with the plant pathogens 1 DBI, 1 DAI and 4 DAI. Disease symptoms for each disease was rated on a 1-9 scale as an approximate measure of disease severity (DS)occurring on the leaves, 1 is no symptoms, 2 is up to 10% of the leaf infected, 3 is 11-20% of the leaf infected, 4 is 21-35%, 5 is 36-50%, 7 is 66-75%, 8 is 76-85%, 9 is greater than 85% of the leaf is infected and showing disease symptoms. The results are shown in Table 1. Glyphosate treatment provided preventative and curative disease severity control for these three diseases, especially those caused by *Cercospora* sp.

TABLE 1

Demonstration of glyphosate disease control on MON89788 to three foliar pathogens

| | Concentration | Aerial Blight | Cercospora Leaf Blight | Frogeye |
|---|---|---|---|---|
| Time of Application | | | | |
| 1 day pre | 1X | 7.1 | 2.8 | 2.7 |
| | 2X | 9.4 | 6.1 | 3.7 |
| | 3X | 8.0 | 3.8 | 3.8 |
| 1 day post | 1X | 5.0 | 2.8 | 3.4 |
| | 2X | 6.4 | 6.4 | 3.3 |
| | 3X | 6.9 | 6.5 | 7.2 |
| 4 days post | 1X | 7.6 | 3.3 | 3.7 |
| | 2X | 4.4 | 3.2 | 5.3 |
| | 3X | 7.9 | 4.9 | 2.3 |
| Inoculated | | | | |
| Control | — | 10.4 | 8.5 | 7.1 |
| $LSD_{(0.05)}$ | | 5.6 | 4.3 | 3.7 |

A high level of control of powdery mildew disease on MON89788 was observed when MON89788 was treated 1 DBI with any of the three rates of glyphosate as illustrated in Table 2. The mean disease severity score for the no spray control was 4.65, the glyphosate treatments provided a high level of disease control at all treatment rates.

TABLE 2

Glyphosate control of powdery mildew disease on MON89788.

| Treatment | lb ae/a | DS Mean |
|---|---|---|
| No spray | 0 | 4.65 |
| Glyphosate | 0.75 (1X) | 1 |
|  | 1.5 (2X) | 1 |
|  | 2.25 (3X) | 1 |
| FLSD (.05) |  | 0.3 |

A deposit of the Monsanto Technology LLC, soybean seed representative of event MON89788 disclosed above and recited in the claims has been made under the Budapest Treaty with the American Type Culture Collection (ATCC), 10801 University Boulevard, Manassas, Va. 20110. The ATCC accession number for MON89788 (also be known as MON19788 or GM 19788) is PTA-6708, deposited May 11, 2005. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. The inventors claim all modifications that are within the spirit and scope of the appended claims.

All publications and published patent documents cited in this specification are incorporated herein by reference to the same extent as if each individual publication or patent application was specifically and individually indicated to be incorporated by reference.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,535,060
U.S. Pat. No. 5,094,945
U.S. Pat. No. 5,310,667
U.S. Pat. No. 5,312,910
U.S. Pat. No. 5,463,175
U.S. Pat. No. 5,554,798
U.S. Pat. No. 5,627,061
U.S. Pat. No. 5,633,435
U.S. Pat. No. 6,040,497
U.S. Pat. No. 6,689,880
U.S. Pat. No. 6,740,488
U.S. Patent Publn. 20030083480
U.S. Patent Publn. 20040018518
U.S. Patent Publn. 20040177399
U.S. Patent Publn. 20050246798
U.S. Patent Publn. 20060021093
U.S. Patent Publn. 20060021094
U.S. Patent Publn. 2005000654442
U.S. Patent Publn. 2003000532758
Frederick et al, *Mycology*, 92:217-227, 2002.
Lewin, In: *Genes V*, Oxford University Press, NY, 1994.
PCT Appln. WO 9200377
Rieger et al., In: *Glossary of Genetics: Classical and Molecular*, 5$^{th}$ Ed., Springer-Verlag, N.Y., 1991.
Sinclair and Backman, In: *Compendium of Soybean Diseases*, 3$^{rd}$ Ed., APS Press, St. Paul, Minn., 106, 1989.
Wrather et al., Online. Plant Health Progress doi:10:1094/PHP-2003-0325-01-RV; 2003.

What is claimed is:

1. A method for controlling a disease in an event MON89788-containing soybean plant comprising,
   (a) identifying a soybean plant as being at risk of disease caused by a pathogen, said soybean plant identified as comprising event MON89788 conferring glyphosate tolerance to the soybean plant, wherein representative soybean seed comprising event MON89788 have been deposited under ATCC accession number PTA-6708; and
   (b) treating the soybean plant with a formulation or mixture comprising glyphosate, whereby the disease is controlled by the glyphosate.

2. The method of claim 1, wherein the disease is caused by a pathogen that is a member of Uredinales, Ustilaginales, Erysiphales, Ascomycetes, Deuteromycetes, or Oomycetes.

3. The method of claim 2, wherein the disease is caused by a *Colletotrichum* sp., *Phakopsora* sp., *Cercospora* sp., *Septoria* sp., *Macrophomina* sp., *Phymatotrichum* sp, *Peronospora* sp., *Microsphaera* sp, *Diaporthe* sp., *Scierotium* sp., *Rhizoctonia* sp., or *Alternaria* sp.

4. The method of claim 3, further comprising,
   (a) identifying the soybean plant as being infected by *Phakopsora pachyrhizi*; and
   (b) applying said formulation or mixture comprising glyphosate to said soybean plant or a portion thereof, whereby the disease is controlled.

5. The method of claim 3, further comprising,
   (a) identifying the soybean plant as being infected by *Rhizoctonia solani*; and
   (b) applying said formulation or mixture comprising glyphosate to said soybean plant or a portion thereof, whereby the disease is controlled.

6. The method of claim 3, further comprising,
   (a) identifying the soybean plant as being infected by *Microsphaera diffusa*; and
   (b) applying said formulation or mixture comprising glyphosate to said soybean plant or a portion thereof, whereby the disease is controlled.

7. The method of claim 3, further comprising,
   (a) identifying the soybean plant as being infected by *Cercospora sojina*; and (b) applying said formulation or mixture comprising glyphosate to said soybean plant or a portion thereof, whereby said disease is controlled.

8. The method of claim 3, further comprising,
(a) identifying the soybean plant as being infected by *Cercospora carotae*; and
(b) applying said formulation or mixture comprising glyphosate to said soybean plant or a portion thereof, whereby said disease is controlled.

9. The method of claim 1, wherein said formulation or mixture comprises a fungicide.

10. The method of claim 9, wherein said fungicide is selected from the group consisting of azoxystrobin, benomyl, blasticidin-S, Bordeaux mixture, tribasic copper sulfate, bromuconazole, captafol, captan, carbendazim, chloroneb, chlorothalonil, copper oxychloride, copper salts, cymoxanil, cyproconazole, cyprodinil, diclomezine, dicloran, difenoconazole, dimethomorph, diniconazole, diniconazole-M, dodine, edifenphos, epoxiconazole, famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate, myclobutanil, ferric methanearsonate, oxadixyl, penconazole, pencycuron, probenazole, prochloraz, propiconazole, pyrifenox, pyroquilon, quinoxyfen, spiroxamine, sulfur, tebuconazole, tetraconazole, thiabendazole, thiophanate-methyl, thiram, triadimefon, triadimenol, tricyclazole, trifloxystrobin, triticonazole, validamycin and vinclozolin and combinations thereof.

11. The method of claim 1, wherein said treatment with glyphosate controls weeds.

12. The method of claim 1, wherein said treatment with glyphosate comprises more than one treatment.

13. The method of claim 1, wherein said treatment with glyphosate is preceded by a treatment with a fungicide.

14. The method of claim 1, wherein said treatment with glyphosate is followed by a treatment with a fungicide.

15. The method of claim 1, wherein seed is harvested from said treated soybean plants.

* * * * *

UNITED STATES PATENT AND TRADEMARK OFFICE
CERTIFICATE OF CORRECTION

PATENT NO. : 7,608,761 B2
APPLICATION NO. : 11/441918
DATED : October 27, 2009
INVENTOR(S) : Baley et al.

It is certified that error appears in the above-identified patent and that said Letters Patent is hereby corrected as shown below:

In claim 3, column 10, line 44, delete "Scierotium" and insert --Sclerotium--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,608,761 B2 | Page 1 of 1 |
| APPLICATION NO. | : 11/441918 | |
| DATED | : October 27, 2009 | |
| INVENTOR(S) | : George Jamie Baley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this
Nineteenth Day of April, 2011

David J. Kappos
*Director of the United States Patent and Trademark Office*